(12) United States Patent
Algar

(10) Patent No.: US 7,175,833 B1
(45) Date of Patent: *Feb. 13, 2007

(54) GLASS COMPOSITION

(75) Inventor: Brian Algar, Ruthin (GB)

(73) Assignee: Teldent Ltd (GB)

( * ) Notice: Subject to any disclaimer, the term of this patent is extended or adjusted under 35 U.S.C. 154(b) by 820 days.

This patent is subject to a terminal disclaimer.

(21) Appl. No.: 10/069,143

(22) PCT Filed: Aug. 14, 2000

(86) PCT No.: PCT/GB00/03141

§ 371 (c)(1),
(2), (4) Date: Jul. 25, 2002

(87) PCT Pub. No.: WO01/12567

PCT Pub. Date: Feb. 22, 2001

(30) Foreign Application Priority Data

Aug. 14, 1999 (GB) .................................. 9919283.3

(51) Int. Cl.
*A61K 8/46* (2006.01)
*A61K 33/42* (2006.01)
*A61Q 11/00* (2006.01)
*A01N 59/26* (2006.01)
*C03C 8/08* (2006.01)

(52) U.S. Cl. .................. 424/57; 424/52; 424/401; 424/435; 424/606; 106/35; 433/215; 433/217.1; 433/226; 433/228.1; 501/24; 501/25; 501/57; 501/58; 501/63; 501/72

(58) Field of Classification Search .................. None
See application file for complete search history.

(56) References Cited

U.S. PATENT DOCUMENTS

| | | | |
|---|---|---|---|
| 4,285,730 A | 8/1981 | Sanford et al. | |
| 4,775,592 A | 10/1988 | Akahane et al. | |
| 4,900,697 A | 2/1990 | Akahane et al. | |
| 5,130,347 A | 7/1992 | Mitra | |
| 5,306,338 A | 4/1994 | Tsunekawa | |
| 5,360,770 A | 11/1994 | Chadwick | |
| 5,520,725 A | 5/1996 | Kato et al. | |
| 5,730,601 A | 3/1998 | Bowman et al. | |
| 5,762,950 A * | 6/1998 | Yli-Urpo et al. | ........... 424/422 |
| 5,814,682 A | 9/1998 | Rusin et al. | |
| 5,871,360 A | 2/1999 | Kato | |
| 5,891,233 A * | 4/1999 | Salonen et al. | ................ 106/35 |
| 5,955,514 A | 9/1999 | Huang et al. | |
| 5,962,550 A | 10/1999 | Akahane et al. | |
| 5,981,620 A | 11/1999 | Hammesfahr et al. | |
| 6,063,832 A | 5/2000 | Yuhda et al. | |
| 6,086,374 A | 7/2000 | Litkowski et al. | |
| 6,191,190 B1 | 2/2001 | Blackwell et al. | |
| 6,214,101 B1 | 4/2001 | Nakaseko | |
| 6,217,644 B1 | 4/2001 | Matsunae et al. | |

FOREIGN PATENT DOCUMENTS

| | | |
|---|---|---|
| EP | 0 509 516 | 3/1997 |
| EP | 0 797 975 | 10/1997 |
| JP | 01 219038 | 9/1989 |
| SU | 313794 | 4/1972 |
| WO | WO 94/19415 | 9/1994 |

OTHER PUBLICATIONS

Toumba, KyraicosJack, *In Vivo and In Vitro Evaluation of a Slow-Release Fluoride Glass for the Prevention of Dental Caries in High-Risk Children*, Published Thesis, University of Leeds, Sep. 1996.

Chemical Abstracts, 112: 184629x, *Glass optical filters capable of correcting transmittance or absorbance in the ultraviolet region*, vol. 112, No. 20, pp. 337, May 1990.

Chemical Abstracts, 6266g, *Glass*, vol. 76, No. 2, p. 6260, Jan. 1972.

* cited by examiner

*Primary Examiner*—Frederick Krass
(74) *Attorney, Agent, or Firm*—Workman Nydegger

(57) ABSTRACT

A glass composition having the general empirical formula given below, expressed in weight percent of the element: P: 16–24, F: 5–30, O: 20–40 and at least one of Na, K, Li or Al in an amount up to a total of 40 wt. % and optionally, up to 5 wt. % of boron and/or silicon. The composition may be used for the treatment and/or prevention of dental caries by providing a slow fluoride releasing device that may be attached to a tooth to release fluoride into the saliva or an individual.

50 Claims, 5 Drawing Sheets

Glass Compositions and Analyses

| Code | Na | P | Al | F | O | K | Ca | Mg | Na+K | F Analysed | Solubility | Melt Temp | Melt Time | Fluoride Retention |
|---|---|---|---|---|---|---|---|---|---|---|---|---|---|---|
| 1 | 21.23 | 20.67 | 6.76 | 19.48 | 31.86 | 0 | 0 | | 21.23 | 10.4 | 149 | 650C | 45MIN | 53.39 |
| 2 | 22.47 | 20.37 | 6.22 | 19.54 | 31.39 | 0 | 0 | | 22.47 | 10.97 | 503 | 650C | 45MIN | 56.14 |
| 3 | 23.68 | 20.08 | 5.69 | 19.6 | 30.94 | 0 | 0 | | 23.68 | 11.81 | 2920 | 650C | 45MIN | 60.26 |
| 4 | 21.54 | 21.18 | 6.26 | 18.37 | 32.64 | 0 | 0 | | 21.54 | 10.94 | 288 | 650C | 45MIN | 59.55 |
| 5 | 21.16 | 20.81 | 5.27 | 18.94 | 32.07 | 0 | 0 | 1.75 | 21.16 | 11.45 | 215 | 650C | 45MIN | 60.45 |
| 6 | 21.23 | 20.67 | 6.76 | 19.48 | 31.86 | 0 | 0 | | 21.23 | 11.42 | 149 | 650C | 45MIN | 58.62 |
| 7 | 21.13 | 20.87 | 4.55 | 18.67 | 32.17 | 0 | 0 | 2.59 | 21.13 | 11.78 | 305 | 650C | 45MIN | 63.10 |
| 8 | 22.88 | 20.27 | 6.04 | 19.56 | 31.25 | 0 | 0 | | 22.88 | 12.01 | 1385 | 650C | 45MIN | 61.40 |
| 9 | 23.28 | 20.17 | 5.87 | 19.59 | 31.09 | 0 | 0 | | 23.28 | 12.15 | 2513 | 650C | 45MIN | 62.02 |
| 10 | 23.21 | 19.68 | 6.22 | 20.56 | 30.33 | 0 | 0 | | 23.21 | 11 | 1816 | 650C | 45MIN | 53.50 |
| 11 | 22.72 | 20.31 | 6.11 | 19.56 | 31.3 | 0 | 0 | | 22.72 | 12.03 | 1962 | 650C | 45MIN | 61.50 |
| 12 | 22.91 | 19.16 | 6.72 | 21.68 | 29.53 | 0 | 0 | 0 | 22.91 | 14.11 | 1684 | 650C | 45MIN | 65.08 |
| 13 | 23.14 | 18.55 | 6.97 | 22.76 | 28.59 | 0 | 0 | 0 | 23.14 | 14.95 | 1715 | 650C | 45MIN | 65.69 |
| 14 | 21.9 | 20.13 | 5.27 | 19.94 | 31.02 | 0 | 0 | 1.75 | 21.9 | 13.22 | 405 | 650C | 45MIN | 66.30 |
| 15 | 22.63 | 19.44 | 5.26 | 20.94 | 29.97 | 0 | 0 | 1.75 | 22.63 | 14.06 | 661 | 650C | 45MIN | 67.14 |
| 16 | 22.13 | 18.76 | 5.26 | 22.3 | 28.92 | 0 | 0 | 2.62 | 22.13 | 14.79 | 685 | 650C | 45MIN | 66.32 |
| 17 | 21.83 | 18.24 | 5.75 | 23.42 | 28.12 | 0 | 0 | 2.64 | 21.83 | 14.86 | 560 | 650C | 45MIN | 63.45 |
| 18 | 14.92 | 20.67 | 6.76 | 18.04 | 31.86 | 7.75 | 0 | 0 | 22.67 | 11.15 | 61 | 650C | 45MIN | 61.81 |
| 19 | 14.29 | 19.79 | 6.25 | 19.71 | 30.5 | 7.68 | 0 | 1.78 | 21.97 | 12.42 | 100 | 650C | 45MIN | 63.01 |
| 20 | 22.07 | 21.09 | 6.01 | 18.34 | 32.5 | 0 | 0 | 0 | 22.07 | 11.2 | 194 | 650C | 45MIN | 61.07 |
| 21 | 21.85 | 21.68 | 5.76 | 17.29 | 33.42 | 0 | 0 | 0 | 21.85 | 10.2 | 574 | 650C | 45MIN | 58.99 |
| 22 | 18.95 | 19.44 | 5.26 | 20.1 | 29.97 | 4.53 | 0 | 1.75 | 23.48 | 12.6 | 389 | 650C | 45MIN | 62.69 |
| 23 | 21.23 | 20.67 | 6.76 | 19.48 | 31.86 | 0 | 0 | | 21.23 | 11 | 130 | 650C | 90MIN | 56.47 |
| 24 | 21.23 | 20.67 | 6.76 | 19.48 | 31.86 | 0 | 0 | | 21.23 | 10.2 | 79 | 650C | 180MIN | 52.36 |
| 25 | 18.95 | 19.44 | 5.26 | 20.1 | 29.97 | 4.53 | 0 | 1.75 | 23.48 | 13.41 | 466 | 600C | 45MIN | 66.72 |

FIG.1

FULL LIST OF GLASS COMPOSITIONS

| CODE | Na | P | Al | F | O | K | Ca | Mg | TOT. | Na+K | F Anal. | Sol. | Rel. | Devit. Grade |
|---|---|---|---|---|---|---|---|---|---|---|---|---|---|---|
| 63 | 19.91 | 18.54 | 8.87 | 24.1 | 28.58 | 0 | 0 | 0 | 100.0 | 19.91 | 10.7 | 45 | 44.40 | |
| 47 | 16.18 | 20.67 | 6.76 | 18.33 | 31.86 | 6.2 | 0 | 0 | 100.0 | 22.38 | 10.2 | 50 | 55.65 | |
| 18 | 14.92 | 20.67 | 6.76 | 18.04 | 31.86 | 7.75 | 0 | 0 | 100.0 | 22.67 | 11.15 | 61 | 61.81 | |
| 62 | 20.25 | 19.09 | 8.33 | 22.92 | 29.41 | 0 | 0 | 0 | 100.0 | 20.25 | 10.8 | 65 | 47.12 | |
| 34 | 20.58 | 19.62 | 7.8 | 21.75 | 30.25 | 0 | 0 | 0 | 100.0 | 20.58 | 11.9 | 78 | 54.71 | |
| 45 | 18.71 | 20.67 | 6.76 | 18.9 | 31.86 | 3.1 | 0 | 0 | 100.0 | 21.81 | 10.7 | 78 | 56.81 | |
| 46 | 17.44 | 20.67 | 6.76 | 18.61 | 31.86 | 4.65 | 0 | 0 | 100.0 | 22.09 | 10 | 79 | 53.73 | |
| 37 | 14.79 | 20.49 | 6.25 | 18.33 | 31.57 | 7.68 | 0 | 0.89 | 100.0 | 22.47 | 9.8 | 80 | 53.46 | |
| 44 | 19.97 | 20.67 | 6.76 | 19.19 | 31.86 | 1.55 | 0 | 0 | 100.0 | 21.52 | 10.6 | 80 | 55.24 | |
| 19 | 14.29 | 19.78 | 6.25 | 19.71 | 30.5 | 7.58 | 0 | 1.78 | 100.0 | 21.87 | 12.42 | 100 | 63.01 | |
| 71 | 18.97 | 20.11 | 6.85 | 19.72 | 31.01 | 3.34 | 0 | 0 | 100.0 | 22.31 | 10.6 | 100 | 53.75 | |
| 33 | 20.91 | 20.15 | 7.27 | 20.61 | 31.06 | 0 | 0 | 0 | 100.0 | 20.91 | 11.4 | 103 | 55.31 | |
| 69 | 11.86 | 18.35 | 7.11 | 20.48 | 28.33 | 13.87 | 0 | 0 | 100.0 | 25.73 | 11.5 | 107 | 56.15 | |
| 70 | 16.66 | 19.54 | 6.93 | 19.97 | 30.14 | 8.76 | 0 | 0 | 100.0 | 25.42 | 10.9 | 110 | 54.58 | |
| 38 | 14.66 | 20.3 | 5.76 | 18.61 | 31.29 | 7.61 | 0 | 1.76 | 100.0 | 22.27 | 10.2 | 128 | 54.81 | |
| 56 | 15.29 | 21.18 | 6.26 | 18.94 | 32.64 | 7.69 | 0 | 0 | 100.0 | 22.98 | 9.9 | 149 | 58.44 | |
| 1 | 21.23 | 20.67 | 6.76 | 19.48 | 31.86 | 0 | 0 | 0 | 100.0 | 21.23 | 10.65 | 158 | 64.67 | |
| 68 | 6.81 | 17.09 | 7.3 | 21.02 | 26.43 | 21.36 | 0 | 0 | 100.0 | 28.17 | 10.3 | 183 | 49.00 | 1 |
| 36 | 21.45 | 20.06 | 7.02 | 20.56 | 30.92 | 0 | 0 | 0 | 100.0 | 21.45 | 12.1 | 186 | 58.85 | |
| 39 | 14.16 | 19.62 | 5.75 | 19.7 | 30.23 | 7.51 | 1.16 | 1.76 | 100.0 | 21.77 | 10 | 189 | 50.76 | |
| 20 | 22.07 | 21.09 | 8.01 | 18.34 | 32.6 | 0 | 0 | 0 | 100.0 | 22.07 | 11.2 | 194 | 61.07 | |
| 35 | 21.67 | 19.45 | 7.27 | 21.65 | 29.97 | 0 | 0 | 0 | 100.0 | 21.67 | 12.4 | 196 | 57.27 | |
| 51 | 22.08 | 18.72 | 7.48 | 22.87 | 28.85 | 0 | 0 | 0 | 100.0 | 22.08 | 13.2 | 211 | 57.72 | |
| 5 | 21.16 | 20.81 | 5.27 | 18.94 | 32.07 | 0 | 0 | 1.75 | 100.0 | 21.16 | 11.45 | 215 | 60.45 | |
| 50 | 22.61 | 18.63 | 7.22 | 22.81 | 28.72 | 0 | 0 | 0 | 100.0 | 22.61 | 12.2 | 234 | 53.49 | |
| 4 | 21.54 | 21.16 | 6.26 | 18.37 | 32.64 | 0 | 0 | 0 | 100.0 | 21.54 | 10.94 | 288 | 59.55 | |
| 41 | 20.83 | 20.38 | 5.03 | 19.75 | 31.41 | 0 | 0 | 2.61 | 100.0 | 20.83 | 11.9 | 297 | 60.25 | |
| 7 | 21.13 | 20.87 | 4.55 | 18.67 | 32.17 | 0 | 0 | 2.59 | 100.0 | 21.13 | 11.78 | 305 | 63.10 | |
| 40 | 14.04 | 19.44 | 5.26 | 19.69 | 28.97 | 7.54 | 2.3 | 1.75 | 100.0 | 21.58 | 11.5 | 315 | 58.41 | |
| 25 | 19.27 | 18.95 | 4.79 | 19.02 | 30.75 | 4.49 | 0 | 1.73 | 100.0 | 23.76 | 11.07 | 370 | 58.20 | |
| 72 | 22.11 | 19.53 | 5.51 | 20.99 | 30.1 | 0 | 0 | 1.76 | 100.0 | 22.11 | 11.9 | 372 | 56.69 | 1 |
| 14 | 21.9 | 20.13 | 5.27 | 19.94 | 31.02 | 0 | 0 | 1.75 | 100.0 | 21.9 | 12.9 | 385 | 64.69 | 1 |
| 22 | 18.95 | 19.44 | 5.26 | 20.1 | 29.97 | 4.53 | 0 | 1.75 | 100.0 | 23.48 | 12.5 | 389 | 62.69 | |
| 65 | 13.05 | 18.08 | 5.26 | 22.21 | 27.87 | 6.03 | 5.75 | 1.75 | 100.0 | 19.08 | 13.5 | 401 | 60.78 | |
| 57 | 15.15 | 20.99 | 5.76 | 18.6 | 32.36 | 9.14 | 0 | 0 | 100.0 | 24.29 | 9.4 | 405 | 56.83 | |
| 42 | 20.64 | 20.2 | 4.55 | 19.74 | 31.14 | 0 | 1.14 | 2.59 | 100.0 | 20.64 | 11.6 | 410 | 58.76 | |
| 64 | 13.05 | 18.08 | 5.28 | 21.85 | 27.87 | 7.54 | 4.6 | 1.75 | 100.0 | 20.59 | 12.1 | 413 | 55.38 | |
| 59 | 21.11 | 22.37 | 5.77 | 16.27 | 34.48 | 0 | 0 | 0 | 100.0 | 21.11 | 7.8 | 436 | 47.94 | |
| 31 | 19.27 | 19.95 | 4.79 | 18.74 | 30.75 | 4.49 | 1.14 | 0.87 | 100.0 | 23.76 | 11.34 | 499 | 60.51 | |
| 2 | 22.47 | 20.37 | 8.22 | 19.54 | 31.39 | 0 | 0 | 0 | 100.0 | 22.47 | 10.97 | 503 | 56.14 | |
| 26 | 19.59 | 20.45 | 4.32 | 17.95 | 31.52 | 4.45 | 0 | 1.72 | 100.0 | 24.04 | 10.73 | 570 | 59.78 | |
| 43 | 20.16 | 19.63 | 4.55 | 20.81 | 30.1 | 0 | 2.27 | 2.59 | 100.0 | 20.16 | 12.1 | 570 | 58.15 | |
| 21 | 21.85 | 21.66 | 5.76 | 17.29 | 33.42 | 0 | 0 | 0 | 100.0 | 21.85 | 10.2 | 574 | 58.99 | |
| 80 | 23.62 | 20.15 | 4.97 | 19.33 | 31.06 | 0 | 0 | 0.86 | 100.0 | 23.62 | 10.2 | 631 | 52.77 | 1 |
| 30 | 19.27 | 19.95 | 4.79 | 18.47 | 30.75 | 4.49 | 2.28 | 0 | 100.0 | 23.76 | 10.99 | 699 | 59.50 | |
| 79 | 23.62 | 20.15 | 4.97 | 19.06 | 31.06 | 0 | 1.13 | 0 | 100.0 | 23.62 | 9.1 | 785 | 47.74 | 1 |
| 28 | 18.78 | 19.28 | 4.78 | 19.73 | 29.71 | 5.98 | 0 | 1.73 | 100.0 | 24.76 | 11.2 | 851 | 56.77 | 1 |
| 27 | 19.35 | 19.28 | 4.78 | 19.87 | 29.71 | 5.23 | 0 | 1.73 | 100.0 | 24.62 | 12.9 | 850 | 64.92 | 1 |
| 32 | 18.78 | 19.27 | 4.78 | 19.19 | 29.71 | 5.98 | 2.28 | 0 | 100.0 | 24.76 | 12.4 | 949 | 64.62 | 1 |
| 29 | 19.11 | 19.79 | 4.31 | 18.66 | 30.48 | 5.93 | 0 | 1.72 | 100.0 | 25.04 | 12.23 | 1006 | 65.54 | |
| 13 | 23.14 | 18.55 | 6.97 | 22.76 | 28.59 | 0 | 0 | 0 | 100.0 | 23.14 | 14.2 | 1038 | 52.39 | |
| 75 | 19.34 | 20.19 | 3.62 | 18.37 | 31.11 | 4.4 | 0 | 2.97 | 100.0 | 23.74 | 11.8 | 1205 | 64.24 | 1 |
| 52 | 14.49 | 20.08 | 5.69 | 17.5 | 30.94 | 11.29 | 0 | 0 | 100.0 | 25.78 | 11 | 1315 | 62.86 | |
| 8 | 22.88 | 20.27 | 6.04 | 19.56 | 31.25 | 0 | 0 | 0 | 100.0 | 22.88 | 12.01 | 1385 | 61.40 | |
| 12 | 22.91 | 19.16 | 6.72 | 21.68 | 29.53 | 0 | 0 | 0 | 100.0 | 22.91 | 14.11 | 1684 | 65.08 | |
| 10 | 23.21 | 19.68 | 6.22 | 20.56 | 30.33 | 0 | 0 | 0 | 100.0 | 23.21 | 11 | 1816 | 53.50 | |
| 58 | 22.16 | 22.17 | 5.28 | 16.22 | 34.18 | 0 | 0 | 0 | 100.0 | 22.16 | 9.2 | 1841 | 55.72 | |
| 11 | 22.72 | 20.31 | 6.11 | 19.56 | 31.3 | 0 | 0 | 0 | 100.0 | 22.72 | 12.03 | 1962 | 61.50 | |
| 9 | 23.28 | 20.17 | 5.87 | 19.59 | 31.09 | 0 | 0 | 0 | 100.0 | 23.28 | 12.15 | 2513 | 62.02 | |
| 3 | 23.68 | 20.08 | 5.69 | 19.6 | 30.94 | 0 | 0 | 0 | 100.0 | 23.68 | 11.81 | 2920 | 60.26 | |
| 76 | 23.83 | 20.33 | 5.45 | 19.06 | 31.33 | 0 | 0 | 0 | 100.0 | 23.83 | 10.9 | 6558 | 57.19 | |
| 77 | 23.97 | 20.58 | 5.21 | 18.53 | 31.72 | 0 | 0 | 0 | 100.0 | 23.97 | 8.3 | 7918 | 44.79 | |
| 78 | 24.19 | 20.82 | 4.97 | 18 | 32.1 | 0 | 0 | 0 | 100.1 | 24.19 | 9.6 | 9285 | 54.44 | |
| 53 | 24.25 | 21.07 | 4.74 | 17.47 | 32.47 | 0 | 0 | 0 | 100.0 | 24.25 | 10.7 | 10429 | 61.25 | |
| 55 | 22.63 | 17.85 | 6.96 | 23.49 | 27.52 | 1.54 | 0 | 0 | 100.0 | 24.17 | | | | 2 |
| 60 | 19.26 | 20.1 | 3.39 | 17.97 | 30.98 | 4.38 | 2.23 | 1.69 | 100.0 | 23.64 | | | | 2 |
| 61 | 19.26 | 20.1 | 3.39 | 18.5 | 30.98 | 4.38 | 0 | 3.38 | 100.0 | 23.64 | | | | 2 |
| 66 | 19.18 | 18.18 | 4.54 | 23.48 | 28.03 | 0 | 2.27 | 4.31 | 100.0 | 19.18 | | | | 2 |
| 67 | 17.73 | 17.85 | 4.54 | 24.5 | 27.51 | 0 | 2.27 | 5.6 | 100.0 | 17.73 | | | | 2 |
| 73 | 23.66 | 18.47 | 6.71 | 22.7 | 28.46 | 0 | 0 | 0 | 100.0 | 23.66 | | | | 2 |
| 74 | 22.83 | 18.01 | 7.48 | 23.91 | 27.76 | 0 | 0 | 0 | 100.0 | 22.83 | | | | 2 |
| 81 | 23.42 | 19.98 | 4.5 | 19.06 | 30.79 | 0 | 2.25 | 0 | 100.0 | 23.42 | | | | 2 |
| 15 | 22.63 | 19.44 | 5.26 | 20.94 | 29.97 | 0 | 0 | 1.75 | 100.0 | 22.63 | | | | 3 |
| 16 | 22.13 | 18.76 | 5.26 | 22.3 | 28.92 | 0 | 0 | 2.62 | 100.0 | 22.13 | | | | 3 |
| 48 | 23.14 | 19.36 | 5.02 | 20.9 | 29.84 | 0 | 0 | 1.74 | 100.0 | 23.14 | | | | 3 |
| 54 | 23.89 | 17.85 | 6.96 | 23.78 | 27.52 | 0 | 0 | 0 | 100.0 | 23.89 | | | | 3 |
| 82 | 23.42 | 19.98 | 4.5 | 19.6 | 30.79 | 0 | 0 | 1.71 | 100.0 | 23.42 | | | | 3 |
| 17 | 21.83 | 18.24 | 5.75 | 23.42 | 28.12 | 0 | 0 | 2.64 | 100.0 | 21.83 | | | | 4 |
| 49 | 23.65 | 19.28 | 4.76 | 20.85 | 29.71 | 0 | 0 | 1.73 | 100.0 | 23.65 | | | | 4 |

FIG.5

GLASS COMPOSITION

BACKGROUND OF THE INVENTION

Applicant claims priority under Rule 371 to PCT/GB00/03141, filed Aug. 14, 2000.

The present invention relates to a glass composition, particularly but not exclusively for the improved treatment and/or prevention of dental caries.

Dental caries consists of demineralization of a tooth caused by bacteria. In the early stages of caries a white spot develops on the tooth and if the disease is not halted and reversed, the enamel surface breaks down to form a lesion. This can then lead to decay and eventually, a fractured tooth. It is well known that development of dental caries may be reduced by means of various factors, such as diet and oral hygiene measures, anti-microbial treatments and the provision of fluoride to the teeth.

Current methods for administering fluoride include the fluoridation of drinking water, the ingestion of fluoride tablets, the incorporation of fluoride into mouth washes, dentifrices and foods, the topical application of fluoride solutions, gels and varnishes and recently, the incorporation of fluoride in dental materials and special devices. These have a variable effect on caries which is unpredictable on an individual basis and is dependent on patient compliance in following the prescribed regimen.

Evidence supports the concept of frequent applications of relatively low concentrations of fluoride ions for the elimination of caries. A sustained and controlled release delivery system could help to achieve this goal. At least three general approaches have been reported for the application of sustained and controlled slow releasing systems, being a sustained release ingested tablet or capsule (Masuhara et al. 1985), incorporation of fluoride in dental cements (McClean & Wilson) and an intra-oral device attached to the teeth Minth et al. 1983). However, none of these devices has proved to be suitable for use. They have either been susceptible to damage, an irritant to the mucosa or non acceptable to the patient.

Glass compositions for attaching to a tooth that release fluoride ions in the mouth to supplement dietary intake of fluoride have proved useful, where normal intake levels of fluoride are insufficient to give maximum reduction in the incidence of caries lesions in teeth.

A glass from which fluoride can be slowly leached was patented by Davidson (U.S. Pat. No. 4,920,082). The glasses described therein consist of silicon dioxide, barium oxides, aluminium oxide and fluoride in specified ranges. However, the maximum fluoride which can be retained in this system is 7% by weight and batch melting temperatures in the range of 1300–1400° C. are generally required. WO88105652 also describes the preparation of novel dental composites that are claimed to release fluoride, incorporating fluorosilicate glass filters, the glass consisting essentially in weight percent of 15–50% $Al_2O_3$, 0–50% CaO, 10–65% $S_iO_2$ and 0–14% F. Again, silicate glass is known to melt at high temperatures which is unfavorable.

The use of phosphate as a glass former has been known for many years. However, the disadvantage of these glasses is that they are easily attacked by water. This property has been exploited for the development of soluble glasses for use in animal health releasing copper, cobalt and selenium to the ruminant animal over 6 to 12 months as the glass dissolves (GB Pat. No. 2116424). A more slowly dissolving glass has been used to provide copper ions in an anti-fouling paint for use on ships. This glass was formulated to dissolve over 5 years (EP App. No. 94906287.1).

Hence, the glass compositions of the prior art have not proved entirely satisfactory for supplementing the dietary intake of fluoride. The low retention of the fluoride means that the release of fluoride is not maintained over a sufficiently long period of time. The low retention would require a relatively large piece of glass to be fixed to the tooth of the patient to provide sufficient levels of fluoride release into the mouth. This would be obtrusive and reduce the appeal of the device to a patient.

SUMMARY

It is an object of the present invention to provide a glass composition, particularly but not exclusively, for the improved treatment and/or prevention of dental caries that aims to overcome the above mentioned drawbacks.

Accordingly, the present invention provides a glass composition having the general empirical formula given below, expressed in weight percent of the element:

P: 16–24
F: 5–30
O: 20–40 and at least one of Na, K, Li or Al in an amount up to a total of 40 wt. % and, optionally, up to 5 wt. % of boron and/or silicon.

Preferably, fluoride and/or oxides of glass modifiers, such as Al, Ca, and Mg, are included in the composition. The fluoride ions are preferably included as compounds such as $AlF_3$, $NaHF_2$, NaF, $CaF_2$, $MgF_2$ or KF.

Ca, Mg, Zn and/or other glass modifiers are preferably included in the composition in an amount 0–10 wt. %, more preferably less than 5 wt. %

The glass compositions of the present invention may be used for the treatment and/or prevention of dental caries. The compositions may be attached to a tooth to provide slow-fluoride releasing devices for releasing fluoride into the saliva of an individual.

The glass compositions of the present invention preferably provide a fluoride retention of at least 45% at a melting temperature of 650° C. over 45 minutes, more preferably at least 60%. Preferably, the glass composition has a low solubility rate thereby allowing fluoride release from the composition for a period of 12–36 months. The solubility of the composition may range from 5–10,000. The required solubility of the glass composition will depend upon the duration of fluoride release required. For example, if the composition is required to release fluoride over a long period, such as 1–2 years the solubility is preferably 100–1100, more preferably 100–1000. However, if fluoride need only be released for a shorter period, such as a few weeks or months, a more soluble glass may be used, for example having solubility of up to 10,000.

The glass compositions of the present invention may be attached to a tooth, for example being attached to a rear molar using standard dental cement or as a powder for adding to dental restorative materials, such as dental amalgams, thereby providing means to supplement fluoride release into saliva to assist in the prevention or reduction of dental caries. The powder may be included in a number of dental materials, such as fissure sealant resins or composite bonding materials to cement bonds and brackets in orthodontic appliances. Powder applications may use glass compositions that are less soluble than those that are attached directly to a tooth, for example having a solubility of 5–100. Such compositions should contain higher levels of glass modifiers and lower alkali levels than those compositions that have a higher solubility.

More preferably, the composition includes a combined weight percent of at least 16% of sodium and potassium, more preferably 19–26 wt. %. Al is preferably included in an amount of at least 3 wt. %, more preferably 4 wt. %, especially 4–10 wt. %.

The composition preferably has at least 25 wt. % oxygen, more preferably 25–35 wt. %, has at least 16 wt. % phosphorus, more preferably 17–23 wt. %, and has at least 12 wt. % F, more preferably 15–25 wt. %. Silicon or boron may replace some of the phosphorus as glass formers. However, preferably only amounts of up to 5% are included to prevent the glass solubility from being unacceptably modified.

The phosphorus may be included in the composition as an oxide, such as $P_2O_5$. The alkali metal compounds may be included as, for example, their oxides or fluorides.

It is to be appreciated that the glass compositions used for the dental appliances should preferably have no, or minimal, devitrification/phase separation. The person skilled in the art of glass making would vary the oxides listed to reduce the tendency of the composition to devitrify in a particular case. For example, the skilled person would know that there are many influences on the tendency of glass compositions to devitrify. For example, glass components with low levels of phosphorus tend to be prone to devitrify and glasses with high levels of magnesium have poor resistance to devitrification. Fluoride glasses are also prone to phase separation.

BRIEF DESCRIPTION OF THE DRAWINGS

The present invention will now be further illustrated by means of the following Examples in which Example 1 investigates the percentage fluoride retention for 25 samples of glass compositions according to the present invention; Example 2 investigates the percentage of fluoride in saliva following attachment of a glass composition of the present invention to a patient's tooth; Example 3 investigates the way that percentage fluoride in slow-releasing glass devices formed from glass compositions according to the present invention affects fluoride release; Example 4 investigates the effect of the location of the fluoride-releasing device on the fluoride levels in saliva in adult human volunteers; Example 5 investigates the effectiveness of powdered glass composition according to the present invention in releasing fluoride into saliva; Example 6 investigates the percentage fluoride retention for 82 samples of glass compositions according to the present invention; Example 7 investigates the effect of varying melt time and temperature on the solubility and fluoride retention of the composition and with reference to the accompanying drawings in which:

FIG. 1 is a table illustrating the percentage fluoride retention of 25 samples investigated in Example 1;

FIG. 5 is a table illustrating the solubility, percentage fluoride retention and extent of devitrification of 82 glass compositions according to the present invention.

DETAILED DESCRIPTION

Figure 2:
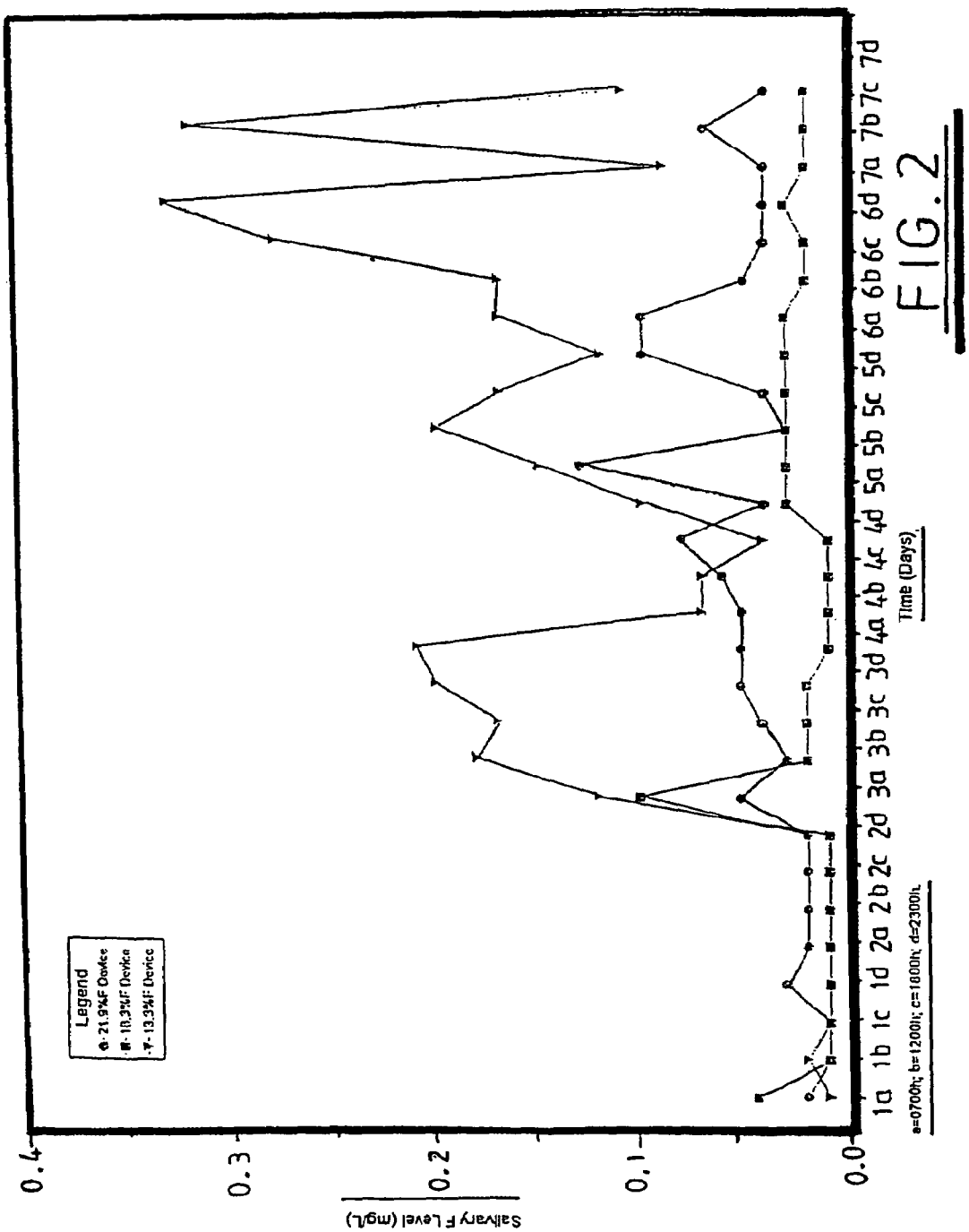
FIG. 2 is a graph illustrating the salivary fluoride levels for compositions of the present invention containing 13.3%, 18.3% and 21.9% fluoride at baseline for 5 days.

In the following examples, the solubility of the glass composition was measured in a standard solubility experiment under controlled conditions. 20 g of the cast glass was placed in percussion mortar and given a single sharp blow with the flat face of a hammerhead. A 0.71 mm sieve was placed on a receiving bottom tray and a 1.0 mm aperture sieve was placed on top of the 0.71 mm. The glass was emptied from the mortar onto the 1 mm sieve and a top pan cover was placed over the top sieve. The sieve and pan were shaken vigorously for thirty seconds and the top pan lid was then removed and the 1.0 mm sieve lifted out. The glass that was left on the top sieve only was poured back into the percussion mortar. The process was then repeated approximately three times to provide sufficient glass for the experiment.

After the third time, the whole pan and sieve assembly was placed onto a sieve vibrator and the vibrator was ran for 5 minutes at amplitude setting 5. The 1 mm sieve was then removed and any glass retained therein disposed of. The 0.71 mm sieve was removed and the glass retained in this sieve was poured into a 100 ml beaker. 20 ml of acetone was added and the beaker was stood in an ultrasonic bath for seven minutes. The 100 ml beaker was then removed from the bath and the acetone was decanted off into the waste acetone bottle.

Another 20 ml of acetone was added to the beaker which was returned to the ultra sonic bath for 1 minute. This was repeated until the acetone appeared clear. Cloudy acetone indicates dust present in the glass, which will cause the solubility results to be high.

After last acetone had been decanted, the beaker was placed in the preheated oven at 110° C. for 30 minutes. The beaker was removed from the oven and re-sieved with 1.0 mm and 0.71 mm sieves.

The solubility test involved weighing accurately approximately 1 g of washed grains and placing the grains in a numbered sinter so that the grains lie on top of the sinter. The mass of grains was recorded on a standard grain solubility record sheet noting the glass batch number and sinter number.

The numbered sinters were mounted in the water bath, set at 40° C., using the correct numbering so as the inlet and outlet tubes were attached to sinter number 1 in which was clipped in the water bath in the left hand retaining clip. Number six sinter was placed in at the rightmost clip. A stop clock was set for 2 hours and a pump was turned on to pass fresh deionized water over the glass samples.

After two hours the water pump and bath were turned off. The tubes were removed from the water bath, carefully decanting off the water from the top section. The tubes were clipped into the stand and approximately 20 ml of acetone was poured into each tube and allowed to drain.

Once the acetone had drained from the tubes, all the tubes were placed together in a 500 ml beaker and returned to the oven for 30 minutes.

A pre-weighed (zeroed) 50 ml beaker was used to weigh the final mass of grains from each tube recording each mass on the standard record sheet. The final solubility is quoted in mg/g/day this being the weight loss in mg divided by the initial weight in g, divided by the time of the test in days.

EXAMPLE 1

FIG. 1 of the accompanying drawings illustrates the composition parameters of glass compositions according to the present invention, labeled 1–25 respectively. The percentage fluoride retained by each composition was calculated from determining the theoretical fluoride percentage of each sample and comparing this to the analyzed level of fluoride found after the glass had been melted. The compositions were recorded as weight percentages of the elements. This was done to ensure the most accurate recording of percentage of fluoride retained. The method often used that involves recording the elements present as oxides and then recording the fluoride as a separate element is incorrect as the fluoride ions are taking the place of oxygen in the glass matrix. Assigning the fluoride ion to any particular element is also incorrect, as the actual location of the fluoride ion is unknown. The method used herein was therefore preferred and conversion to other older systems is easily achieved for comparison purposes.

The percentage fluoride retained by the samples is given in FIG. 1 of the accompanying drawing.

EXAMPLE 2

The percentage of fluoride released into saliva following attachment of a glass composition of the present invention to a tooth was investigated.

The batch components using compositions according to the present invention were thoroughly mixed to ensure a homogeneous melt and loaded into platinum crucibles. The crucibles were then placed in an electric melting furnace at temperatures from 600–650° C., for times of up to 60 minutes to achieve good melting. The crucibles were removed from the furnace and the glass cast onto a molding plate containing a number of circular holes of 4 mm in diameter and 6 mm in depth. The glass was rolled to force it into these cavities and when solidified it was removed from the plate and transferred to an annealing oven to slowly cool and remove any residual stress.

Before use, the devices were smoothed of any rough edges with a sharp diamond burr. Three tests were carried out with human subjects and the results are reported in Tables I–III below. The device was attached to the buccal aspect of the first maxillary permanent molar because of its nearness to the opening of the parotid gland. It was felt that the salivary flow would help to distribute the fluoride to other parts of the mouth. The tooth was cleaned using a fluoride-free prophylaxis paste. After cleaning, the tooth was washed, dried and the buccal surface etched for one minute with the etch available in the composite kit. (Prisma Fil-Predosed High Density Composite, The L.d. Chalk Company, Division of Dentsply International Inc., Milford, Del. 19963, U.S.A.). The glass was etched for twenty seconds. Both were washed, dried and a thin layer of a light cured bond from the composite kit brushed on the tooth and the glass. The glass, held by tweezers, was adapted to the tooth and cured by visible light. While temporarily held in place, a layer of light cured composite was adapted around the glass using a plastic instrument. This composite helps to retain the glass, blocks out any under cuts and makes the whole device smooth to the tongue. Once cured, the glass and composite were further smoothed with a white stone burr and a layer of fissure sealant placed on the composite and cured to give a smoother surface. Control of moisture was very important throughout this procedure. Care was taken not to cover the exposed releasing surface of the glass with any composite, bond or fissure sealant.

In these studies, efforts were made to ensure that the fluoride in saliva could be accurately and repeatedly determined. The method employed was that of Taves (Separation of fluoride by rapid diffusion using hexamethyldisiloxane, Tahanta 15, 969–974, 1968), in which fluoride was diffused from the samples using hydrochloric acid saturated with hexamethyldisiloxane $(CH_3)_3SiOSi(CH_3)_3$ (HMDS). Fluoride was collected in sodium hydroxide before its determination by a fluoride ion electrode.

For each sample of saliva, between 1.0 and 2.0 g (depending on the sample size) was weighed into a 60×15 mm polystyrene petri dish (Falcon Plastics Cat No. 1007, Fahrenheit Lab. Supplies, Leeds). This avoided the difficulty of trying to accurately pipette this viscous material. Distilled water was added to make the final volume of 3.0 ml. Polystyrene tube caps (Falcon Plastics Cat No. 2051, Fahrenheit Lab. Supplies, Leeds.), with the rims reduced by a half, were placed in the center of each dish.

0.1 ml of 1.65M NaOH containing P-nitrophenol and phenophthalein as an indicator was added to the center of each well to ensure that the trap remained alkaline and therefore was able to trap the fluoride. An alkaline trap remained pale yellow in color while an acidified trap turned pink. The lids were then sealed on the petri dishes using petroleum jelly around the rims. Finally 1.0 ml of 6.0M HCl with HMDS was added to each dish via a small hole previously made in the lid and the hole sealed immediately with petroleum jelly and a square of sealing tissue.

The samples were placed on a rotary shaker at 200 rotations/minute and left to diffuse overnight which was usually 16 hours. The following morning the lids were pried off and a note made of any of the dishes which had not formed a vacuum since loss of the vacuum had been shown in preliminary tests to be an indicator that fluoride had been lost from the system. Each of the caps were removed and placed in an oven at 100° C. until the NaOH had become crystalline.

After drying the NaOH the caps were placed on their test tubes and shaken with 0.34M acetic acid to dissolve the crystals and bring the pH to 5.2 for its determination by a combination fluoride ion electrode. Fluoride standards of 0.05, 0.1, 0.5, 1.0 and 5.0 μm/ml F were prepared in identically buffered solutions to the sample solutions and were used to construct a standard curve. The fluoride concentrations in the unknown diffused samples were measured from this curve using an Orion combination fluoride ion electrode and Orion 920A Ionanalyser (Orion Research Inc., Cambridge, Mass.). From the concentrations of the diffused solutions, the concentrations of fluoride in the original sample were calculated.

In all analyses, known fluoride standards and blanks were also diffused to determine the percentage diffusion that was occurring. The level of diffusion varied between 96.0 and 108% where a vacuum had been maintained. When known samples of fluoride solutions were diffused, the standard deviation between the recoveries was usually less than 1.0%.

Fluoride blanks were also run in this system. These included HCl—HMDS+water or NaOH alone. Fluoride was not measurable in the water or the HCl after it had been saturated with the HMDS. It appeared that the NaOH was the main contributor to the small blank of 0.002 μg/ml F.

A check was made to determine if the fluoride concentration changed if the analyses were not done on the day of collection since it was possible that there would be too many samples to handle on some of the days when a study of salivary fluoride was being carried out and/or because laboratory facilities were not available every day. Therefore, duplicate analyses were carried out on samples which had been kept up to 7 hours at room temperature and on samples which had been stored up to 10 days at −12° C. The former was to check if study subjects could take part in collecting saliva while going about their normal work and bring the samples for analysis at the end of the collection period. The latter was to allow for the collection and storage of saliva samples when laboratory facilities were not available or for when the numbers of samples had built up beyond those which could be readily handled. No differences were found in the fluoride levels analyzed immediately, after up to 7 hours or after 10 days at −12° C.

The recovery of fluoride and reproducibility of the method were checked by using known standards and by carrying out repeat analyses on the same samples. The results of these preliminary analyses are shown in Table I below.

TABLE I

Reproductability and Recovery of Fluoride After Diffusion of Samples in HMDS-HCl

| Sample No. 3 | (ml solution) | No. of Tests | Known F[1] F | Determined F F | SD[3] | Recovery (%) |
|---|---|---|---|---|---|---|
| 1 | 1 | 4 | 0.05 | 0.045 | ±0.002 | 90 |
| 2 | 1.0 | 4 | 0.1 | 0.092 | ±0.010 | 92 |
| 3 | 0.5 | 6 | 0.5 | 0.475 | ±0.030 | 95 |
| 4 | 0.5 | 3 | 1.0 | 0.940 | ±0.010 | 94 |
| 5 | 0.2 | 2 | 5.0 | 4.900 | ±0.008 | 98 |
| 6 | Dist H$_2$O | 10 | NIL | <0.005 | ±0.000 | |
| 7 | Whole resting saliva | 6 | Unknown | 0.010 | ±0.003 | |
| 8 | Whole resting saliva | 10 | Unknown | 0.015 | ±0.005 | |

[1]F = Fluoride concentration in μg/ml
[2]Samples 1, 4 and 7 were from one standard solution or one saliva source and analyzed at the same time.
2, 5 and 6 were from known solutions or distilled H$_2$O prepared and analyzed at different times.
3 and 8 were from one solution or one saliva source analyzed at different times.
[3]SD = Standard deviation.

The results show that the recovery of fluoride by the test system was better than 90%. There was therefore an error of only 10%, which was thought to be very good, and tem was acceptable.

Table II below shows the fluoride concentration in saliva of a subject fitted with a device made from glass composition 16 in FIG. 1 of the accompanying drawing. A marked high increase in fluoride level in saliva was observed within the first three days. This level then settled down to a steady 0.025–0.035 μg/ml, giving on average a three-fold increase from the 0.09–0.12 μg/ml base line. The effect of the device was still clearly seen even after a year and a half in place in the subject.

TABLE II

Fluoride Concentration in μg/ml. of Saliva for Subject Fitted with Glass 16

| | | Fluoride Concentration μg/ml |
|---|---|---|
| Base line | Day 1 | 0.012 |
| | Day 2 | 0.009 |
| Treatment | Day 1 | 0.063 |
| | Day 2 | 0.039 |
| | Day 3 | 0.069 |
| | Day 4 | 0.031 |

TABLE II-continued

Fluoride Concentration in μg/ml. of Saliva for Subject Fitted with Glass 16

| | | Fluoride Concentration μg/ml |
|---|---|---|
| | Day 5 | 0.028 |
| | Day 6 | 0.037 |
| | Week 1 | 0.036 |
| | Week 2 | 0.025 |
| | Week 3 | 0.024 |
| | Month 1 | 0.030 |
| | Month 2 | 0.030 |
| | Month 3 | 0.036 |
| | Month 4 | 0.038 |
| | Month 5 | 0.034 |
| | Month 6 | 0.033 |
| | Year 1 | 0.03 |
| | Year 1.5 | 0.05 |

Table III below shows the averaged fluoride concentration in saliva of two subjects fitted each with a device made from composition 14 in FIG. 1 of the accompanying drawing. A marked high increase in fluoride level in saliva was again observed at the start but this time only for the first two days. This level then settled down to a steady 0.02–0.025 μg/ml, giving on average a two and a half fold increase from the 0.009 μg/ml base line. The device was still effective up to the four month point when it was removed.

TABLE III

Averaged Fluoride Concentration in μg/ml of Saliva for Two Subjects Fitted with Glass 14

| | | Fluoride Concentration g/ml. |
|---|---|---|
| Base line | Day 1 | 0.009 |
| | Day 2 | 0.009 |
| Treatment | Day 1 | 0.056 |
| | Day 2 | 0.053 |
| | Day 3 | 0.023 |
| | Day 4 | 0.024 |
| | Day 5 | 0.024 |
| | Day 6 | 0.035 |
| | Week 1 | 0.025 |
| | Week 2 | 0.022 |
| | Week 3 | 0.023 |
| | Month 1 | 0.025 |
| | Month 2 | 0.017 |
| | Month 3 | 0.022 |
| | Month 4 | 0.022 |

Table IV below shows the averaged fluoride concentration in saliva of four subjects fitted each with two devices made from glass composition 14 in FIG. 1 of the accompanying drawing. Again the level of fluoride was high for the first three but then settled down to around the 0.035 μg/ml, a level which was a three and a half fold increase over the base line. There was also an unusually high level of fluoride recorded at weeks 1 and 2.

TABLE IV

Averaged Fluoride Concentration in μg/ml of Saliva for Four Subjects Each Filled with Two Devices of Glass 15

| | | Fluoride Concentration μg/ml |
|---|---|---|
| Base Line | Day 1 | 0.01 |
| | Day 2 | 0.01 |
| Treatment | Day 1 | 0.043 |
| | Day 2 | 0.053 |

TABLE IV-continued

Averaged Fluoride Concentration in μg/ml of Saliva for
Four Subjects Each Filled with Two Devices of Glass 15

| | Fluoride Concentration μg/ml |
|---|---|
| Day 3 | 0.045 |
| Day 4 | 0.034 |
| Day 5 | 0.041 |
| Day 6 | 0.032 |
| Week 1 | 0.067 |
| Week 2 | 0.054 |
| Week 3 | 0.033 |
| Month 1 | 0.036 |
| Month 2 | 0.033 |
| Month 3 | 0.035 |
| Month 4 | 0.033 |
| Month 5 | 0.035 |
| Month 6 | 0.032 |

The results clearly show that high levels of fluoride can be retained by the glass compositions of the present invention, up to 15% in the compositions included in FIG. 1, with acceptable levels of fluoride retention (up to 67% in the compositions of FIG. 1). Additionally, melting temperatures can be kept low, generally at 650° C. or less. The glass compositions also allow fluoride to be released from the glasses for up to at least 1½ years, as illustrated in Table II. Furthermore, the level of fluoride released from the composition can be adjusted by changes in retained fluoride, glass composition and the number of devices used, as shown in FIG. 1 and Tables II to IV. Hence, the compositions of the present invention provide a glass containing fluoride for insertion into the mouth for a slow continuous release of fluoride ions, the glass being fitted either by attachment of a formal article of the glass to a tooth, being held in place by a dental plate or by incorporation of glass in a powder form as a dental restorative.

EXAMPLE 3

An investigation was conducted to determine the salivary fluoride levels that could be achieved by increasing the percentage fluoride in three examples of glass compositions according to the present invention. The three glass devices were made with either 13.3%, 18.3% or 21.9% retained fluoride and had the following compositions:

| Retained Fluoride: | 13.3% | 18.3% | 21.9% |
|---|---|---|---|
| Na | 21.23 | 19.38 | 19.68 |
| P | 20.67 | 19.50 | 17.84 |
| Al | 6.76 | 8.94 | 9.90 |
| F | 19.48 | 22.12 | 25.08 |
| O | 31.86 | 30.06 | 27.49 |

The average weight of the glass devices was 82.25 mg and the quantity of fluoride in the three devices was 11.94, 15.05 and 18.01 mg F for the devices respectively. Three adult volunteers used a fluoride-free toothpaste for two weeks prior to and for the duration of the study. The glass devices were attached to the buccal surfaces of maxillary first permanent molars using an acid etch composite resin technique. Saliva samples were collected in 30 ml plastic specimen containers for two minutes as whole resting saliva, four times per day without stimulation at 0700, 1200, 1800 and 2300 hrs each day. Saliva samples were collected for two days prior to attachment of the glass devices, to establish baseline saliva fluoride levels, further saliva samples were collected for the first five days, and then weekly for one month. All saliva samples were analyzed for fluoride using a fluoride ion-specific electrode after acid diffusion according to the method of Taves (1968).

Figure 3:
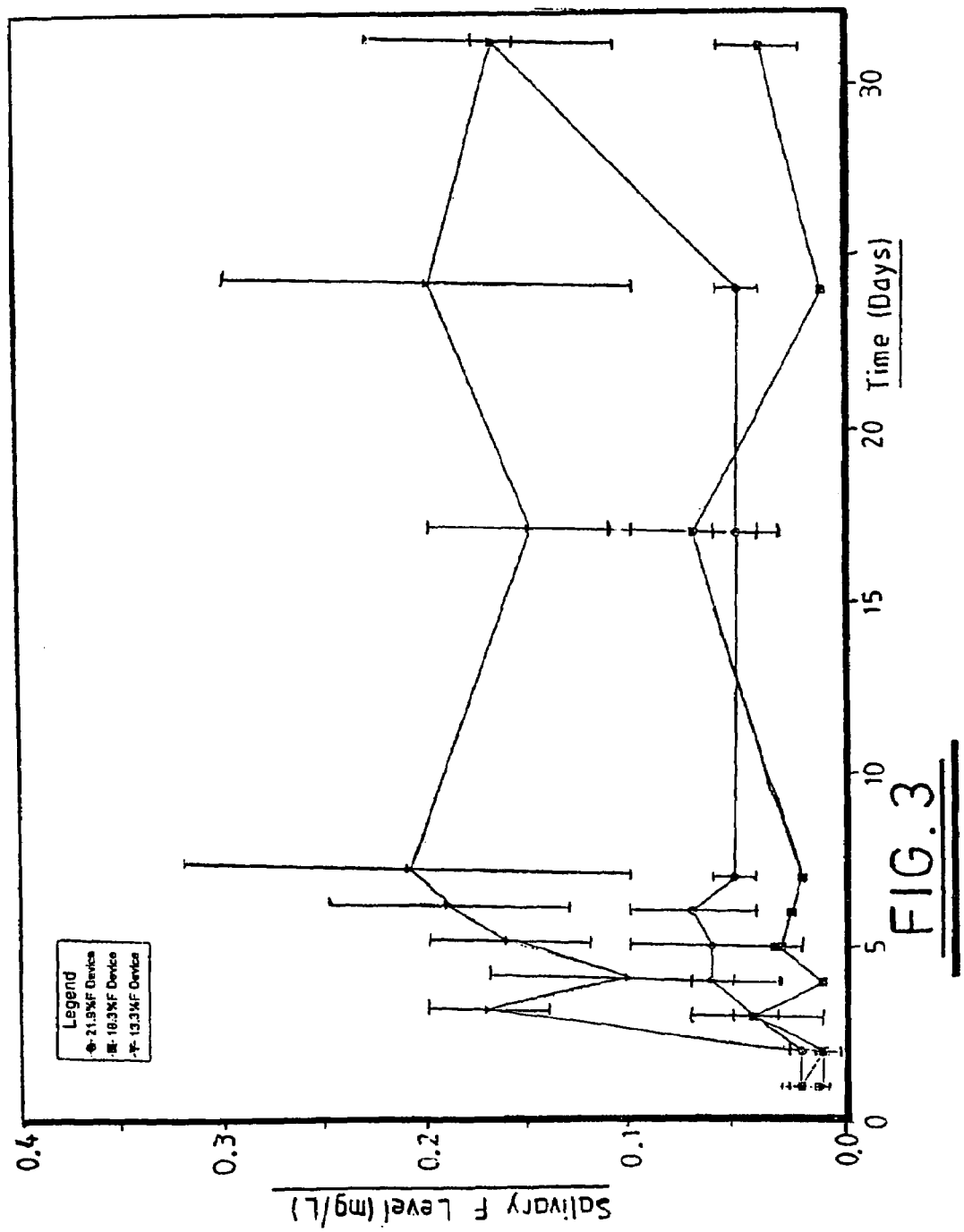
FIG. 3 is a graph illustrating the mean daily salivary fluoride levels for compositions according to the present invention containing 13.3%, 18.3% and 21.9% fluoride at baseline for one month.

The results of the daily and the mean daily fluoride release from the 13.3%, 18.3% and 21.9% fluoride devices for a period of one month are shown in Tables V and VI respectively. FIG. 2 illustrates the fluoride release throughout each day (i.e. four collection times per day) for baseline and the first five days after attachment of the devices. FIG. 3 illustrates the mean daily fluoride release for the three devices for the one month period. Fluoride levels were (mean, range mg/L) 13.3%=0.17, 0.04–0.37; 18.3%=0.03, 0.01–0.12; 21.9% 0.07, 0.03–0.25. Salivary fluoride levels achieved were greater for the 13.3% than the other two fluoride slow-release glass devices.

TABLE V

Daily Fluoride Levels (mg/L) for 3 Adult Volunteers with 13.3%, 18.3% and 21.9% Fluoride Glass Devices for One Month

| Day | | 13.3% Glass (mg/L F) | 18.3% Glass (mg/L F) | 21.9% Glass (mg/L F) |
|---|---|---|---|---|
| Baseline | 1a = 0700 h | 0.01 | 0.04 | 0.02 |
| | 1b = 1200 h | 0.02 | 0.01 | 0.01 |
| | 1c = 1800 h | 0.01 | 0.01 | 0.01 |
| | 1d = 2300 h | 0.01 | 0.01 | 0.03 |
| Baseline | 2a | 0.01 | 0.01 | 0.02 |
| | 2b | 0.01 | 0.01 | 0.02 |
| | 2c | 0.01 | 0.01 | 0.02 |
| | 2d | 0.01 | 0.01 | 0.02 |
| | Means ± SD | 0.01 ± 0.003 | 0.01 ± 0.009 | 0.02 ± 0.006 |
| Day | 1a | 0.12 | 0.10 | 0.05 |
| | 1b | 0.18 | 0.02 | 0.03 |
| | 1c | 0.17 | 0.02 | 0.04 |
| | 1d | 0.20 | 0.02 | 0.05 |
| Day | 2a | 0.21 | 0.01 | 0.05 |
| | 2b | 0.07 | 0.01 | 0.05 |
| | 2c | 0.07 | 0.01 | 0.06 |
| | 2d | 0.04 | 0.01 | 0.08 |
| Day | 3a | 0.10 | 0.03 | 0.04 |
| | 3b | 0.15 | 0.03 | 0.13 |
| | 3c | 0.20 | 0.03 | 0.03 |
| | 3d | 0.17 | 0.03 | 0.04 |
| Day | 4a | 0.12 | 0.03 | 0.10 |
| | 4b | 0.17 | 0.03 | 0.10 |
| | 4c | 0.17 | 0.02 | 0.05 |
| | 4d | 0.28 | 0.02 | 0.04 |
| Day | 5a | 0.33 | 0.03 | 0.04 |
| | 5b | 0.09 | 0.02 | 0.04 |
| | 5c | 0.32 | 0.02 | 0.07 |
| | 5d | 0.11 | 0.02 | 0.04 |
| Week | 2a | 0.17 | 0.08 | 0.05 |
| | 2b | 0.075 | 0.12 | 0.04 |
| | 2c | 0.15 | 0.04 | 0.04 |
| | 2d | 0.21 | 0.03 | 0.07 |
| Week | 3a | 0.375 | 0.01 | 0.04 |
| | 3b | 0.10 | 0.01 | 0.04 |
| | 3c | 0.17 | 0.01 | 0.05 |
| | 3d | 0.17 | 0.01 | 0.06 |
| Week | 4a | 0.17 | 0.08 | 0.20 |
| | 4b | 0.17 | 0.04 | 0.10 |
| | 4c | 0.15 | 0.02 | 0.25 |
| | 4d | 0.19 | 0.02 | 0.12 |
| | Means ± SD | 0.17 ± 0.07 | 0.03 ± 0.026 | 0.07 ± 0.05 |

TABLE VI

Mean (±SD) Daily Fluoride Levels (mg/L) for 3 Adult Volunteers with 13.3%, 18.3% and 21.9% Glass Device for One Month

| Day | 13.3% Glass (mg/L F) | 18.3% Glass (mg/L F) | 21.9% Glass (mg/L F) |
|---|---|---|---|
| Baseline 1 | 0.01 | 0.02 | 0.02 |
| Baseline 2 | 0.01 | 0.01 | 0.02 |
| Mean ± SD | 0.01 ± 0.003 | 0.01 ± 0.009 | 0.02 ± 0.006 |
| Day 1 | 0.17 ± 0.03 | 0.04 ± 0.03 | 0.04 ± 0.01 |
| Day 2 | 0.10 ± 0.07 | 0.01 ± 0.01 | 0.06 ± 0.01 |
| Day 3 | 0.16 ± 0.04 | 0.03 ± 0.01 | 0.06 ± 0.04 |
| Day 4 | 0.19 ± 0.06 | 0.03 ± 0.01 | 0.07 ± 0.03 |
| Day 5 | 0.21 ± 0.11 | 0.02 ± 0.01 | 0.05 ± 0.01 |
| Week 2 | 0.15 ± 0.05 | 0.07 ± 0.04 | 0.05 ± 0.01 |
| Week 3 | 0.20 ± 0.10 | 0.01 ± 0.01 | 0.05 ± 0.01 |
| Week 4 | 0.17 ± 0.01 | 0.04 ± 0.02 | 0.17 ± 0.06 |
| Mean ± SD | 0.17 ± 0.07 | 0.03 ± 0.026 | 0.07 ± 0.05 |

Pooled human unstimulated saliva was collected from normal adult volunteers as whole resting saliva and divided into 15 aliquots of 3 ml in plastic tubes. The saliva samples were used for the study immediately following the collection period. Five samples of each of the three glass devices containing 13.3%, 18.3% and 21.9% fluoride were placed into each of the plastic tubes containing the aliquot of the pooled saliva. These were placed on a Ika-Vibrax VXR rotary shaker at 200 rotations per minute and left for two hours. One ml aliquots were taken from each tube in duplicate and analyzed for fluoride together with duplicate samples of the pooled saliva using a fluoride ion-specific electrode after acid diffusion according to the method of Taves (1968).

The results of the in vitro salivary fluoride levels of the 13.3%; 18.3% and 21.9% F devices shaken for two hours in pooled human saliva is shown in Table VII. The level of fluoride release was again greater for the 13.3% device.

TABLE VII

In vitro Salivary Fluoride Levels (mg/L) of 13.3%, 18.3% and 21.9% Fluoride Glass Devices Shaken for 2 Hours with Pooled Adult Human Saliva

| Pooled Saliva (mg/L F) | 13.3% Glass (mg/L F) | 18.3% Glass (mg/L F) | 21.9% Glass (mg/L F) |
|---|---|---|---|
| 0.06 | 2.21 | 1.52 | 1.02 |
| 0.06 | 2.07 | 1.41 | 1.05 |
| 0.06 | 2.19 | 1.50 | 0.99 |
| 0.06 | 2.20 | 1.55 | 0.99 |
| 0.06 | 2.22 | 1.48 | 1.01 |
| Mean ± SD 0.06 ± 0.00 | Mean ± SD 2.18 ± 0.05 | Mean ± SD 1.49 ± 0.05 | Mean ± SD 1.01 ± 0.02 |

The results of the study of fluoride release from the slow-release devices containing increasing amounts of fluoride gave surprising results. Salivary fluoride levels achieved were surprisingly greater for the 13.3% device than the other two higher percentage fluoride glasses. It had been expected that the higher fluoride concentration glass device would yield the highest salivary fluoride levels. The greater fluoride release from the 13.3% device was confirmed from the in vitro study. A post-study review showed that due to manufacturing considerations the 18.3% and 21.9% devices contained a mixture of aluminum and sodium fluoride, whereas the 13.3% device contained sodium fluoride alone. Aluminum reacts with fluoride strongly to form aluminum fluoride, which is much less soluble than other forms of fluoride. Therefore, the fluoride glass devices containing aluminum fluoride were in comparison to the sodium fluoride glass device, relatively insoluble with respect to fluoride release. Therefore, fluoride was more available from the 13.3% fluoride device which was felt to be better as a slow-releasing device for the future studies.

EXAMPLE 4

It was felt necessary to determine which tooth sites were most appropriate for attachment of the devices and for fluoride release. Volunteers used the same fluoride-free toothpaste for two weeks prior to and for the duration of the study. Four adult volunteers each had fluoride glass devices attached to the buccal surfaces of their maxillary right first permanent molar teeth. Another four adult volunteers had fluoride glass devices attached bilaterally to the buccal surfaces of their maxillary right and left first permanent molar teeth. Finally, four adult volunteers had fluoride glass devices attached to the buccal surfaces of their mandibular right first permanent molar teeth. Finally, four adult volunteers had fluoride glass devices attached to the lingual surfaces of their mandibular right and left permanent canine teeth. All of the fluoride glass devices contained 13.3% fluoride, and were attached to the tooth sites using the acid etch composite technique.

Table VIII shows the salivary fluoride levels of the volunteers at baseline and at one day, one week and two weeks post-insertion of the glass devices. The mean salivary fluoride levels were 0.01–0.02 mg/L F at baseline and 0.17–0.18 mg/L F post insertion of the F devices.

TABLE VIII

Mean Salivary Fluoride Levels of Adult Human Volunteers Whilst Wearing Lower Appliances with 13.3% Fluoride Glass Devices Attached

| Day | Volunteer 1 (mg/L F) | Volunteer 2 (mg L F) | Volunteer 3 (mg/L F) | Volunteer 4 (mg/L F) |
|---|---|---|---|---|
| Baseline | 0.01 | 0.01 | 0.02 | 0.01 |
| Day 1 | 0.18 | 0.17 | 0.18 | 0.18 |
| Week 1 | 0.17 | 0.17 | 0.18 | 0.18 |
| Week 2 | 0.17 | 0.18 | 0.18 | 0.17 |
| Mean(±SD) | 0.17(±0.01) | 0.17(±0.01) | 0.18(±0.01) | 0.18(±0.02) |

The above findings suggest that fluoride is distributed around the mouth from these devices and does not remain site specific.

EXAMPLE 5

Samples of the glass composition in powdered form were provided, the samples were of two grain sizes as follows:
1) <38 microns
2) <106 microns
and of three relative solubilities as follows:
1) 1
2) 10
3) 100
The three samples had the following compositions:

| Relative Solubility: | 1 | 10 | 100 |
|---|---|---|---|
| Na | 18.23 | 21.23 | 25.92 |
| P | 20.85 | 20.67 | 20.39 |
| Al | 8.41 | 6.76 | 4.18 |

-continued

| Relative Solubility: | 1 | 10 | 100 |
|---|---|---|---|
| F | 20.38 | 19.48 | 18.08 |
| O | 32.13 | 31.86 | 31.43 |

0.1 g of each of the powdered fluoride glass samples was mixed with 1.0 g of Aurafill light curing composite restorative material (Gray shade, Johnson & Johnson) and placed in a 5 mm diameter plastic mould and light cured for 60 seconds to provide fluoride glass-composite pellets. Duplicate pellets of each of the powdered glass samples were prepared with the composite material and duplicate pellets of composite material alone were also prepared to act as controls. A total of 14 pellets were prepared. Each pellet was weighed (mean weight 0.28 g±0.01 S.D.) and the pellets were placed in plastic tubes (Falcon Code 2051) with 3 ml of distilled water and left for 24 hours. One ml aliquots were analyzed for fluoride in duplicate after acid diffusion according to the method of Taves (1968). The pellets were then replaced in their plastic tubes containing fresh 3 ml aliquots of distilled water. One ml aliquots were analyzed for fluoride daily (except at weekends) for a period of one month.

Figure 4:
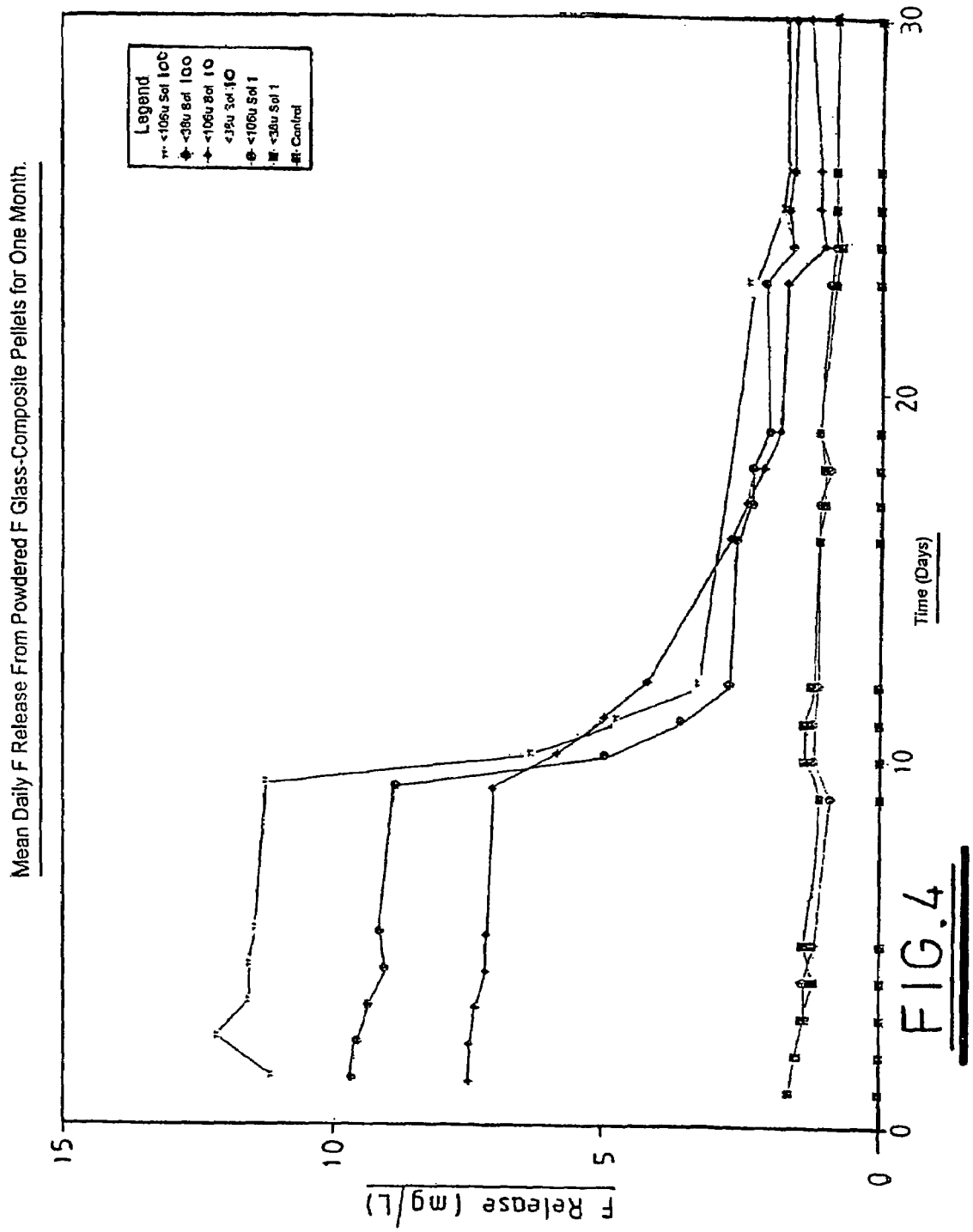
FIG. 4 is a graph illustrating the mean daily fluoride release for powdered fluoride glass composite pellets according to the present invention for one month.

The in vitro results of the daily fluoride release for a period of one month of the powdered forms of the fluoride glass, of two grain sizes (<38 microns and <106 microns) and of three relative solubilities (1, 10 and 100), when mixed with composite material are shown in Table IX below and illustrated in FIG. 4. Table X below shows the in vitro results when the powdered fluoride glass-composite mixes were left undisturbed for a period of four weeks. Fluoride was released at mean levels ranging from 1.5–12.2 mg/L daily at commencement, and 0.8–1.8 mg/L at the end of the study. The <38 micron grain size with a relative solubility of 1 showed consistent fluoride release of 0.7–1.5 mg/L daily throughout the study.

Powdered F glass samples:
<38 microns, Relative Solubility=1
<106 microns, Relative Solubility=1
<38 microns, Relative Solubility=10
<106 microns, Relative Solubility=10
<38 microns, Relative Solubility=100
<106 microns, Relative Solubility=100

0.1 g of each of the powdered F glass samples was mixed with 1.0 g of Aurafill® composite material.

Mean Weight (±SD) of Pellets=0.28 g (±0.01)

TABLE X

In vitro Mean F Levels (mg/L) for Powdered F Glass-Composite Pellets Left Undisturbed for Four Weeks

| F Glass-Composite Mixture | Mean (±SD) F Release (mg/L F) |
|---|---|
| Control | 0.0 ± 0.0 |
| 1) <38 microns, Relative Solubility = 1 | 12.9 ± 2.6 |
| 2) <106 microns, Relative Solubility = 1 | 9.0 ± 1.1 |
| 3) <38 microns, Relative Solubility = 10 | 38.0 ± 1.6 |
| 4) <106 microns, Relative Solubility = 10 | 44.3 ± 3.8 |
| 5) <38 microns, Relative Solubility = 100 | >100.0 |
| 6) <106 microns, Relative Solubility = 100 | >100.0 |

0.1 g of each of the powdered F glass samples was mixed with 1.0 g of Aurafill® composite material.

Mean Weight (±SD) of Pellets=0.28 g (±0.01)

The powdered form of the fluoride glass having <38 micron grain size with a relative solubility of 1 has great potential for incorporation into a number of dental materials, with preventive actions in a number of dental disciplines. It maybe added to dental restorative materials for routine conservation, with the aim of preventing secondary caries around the margins of restorations. In addition, it will provide a source of long term intra-oral fluoride for prevention of new carious lesions. Incorporation within fissure

|  | Control (mg/LF) | <38 μm Sol 1 (mg/LF) | <106 μm Sol 1 (mg/LF) | <38 μm Sol 1 (mg/LF) | <106 μm Sol 10 (mg/LF) | <38 μm Sol 100 (mg/LF) | <106 μm Sol 100 (mg/LF) |
|---|---|---|---|---|---|---|---|
| Day 1 | 0.0 | 1.5 ± 0.0 | 1.5 ± 0.1 | 6.6 ± 0.2 | 7.5 ± 0.3 | 9.7 ± 0.2 | 12.2 ± 0.3 |
| Day 2 | 0.0 | 1.4 ± 0.2 | 1.4 ± 0.1 | 6.5 ± 0.1 | 7.5 ± 0.2 | 9.6 ± 0.1 | 12.2 ± 0.2 |
| Day 3 | 0.0 | 1.3 ± 0.1 | 1.3 ± 0.1 | 6.5 ± 0.2 | 7.4 ± 0.2 | 9.4 ± 0.3 | 11.6 ± 0.3 |
| Day 4 | 0.0 | 1.2 ± 0.1 | 1.3 ± 0.1 | 6.2 ± 0.1 | 7.2 ± 0.1 | 9.1 ± 0.2 | 11.6 ± 0.2 |
| Day 5 | 0.0 | 1.3 ± 0.2 | 1.2 ± 0.1 | 6.3 ± 0.1 | 7.2 ± 0.1 | 9.2 ± 0.1 | 11.5 ± 0.2 |
| Day 8* | 0.0 | 2.6 ± 0.1 | 2.4 ± 0.1 | 10.4 ± 0.2 | 13.1 ± 0.1 | 15.6 ± 0.2 | 18.3 ± 0.2 |
| Day 9 | 0.0 | 1.1 ± 0.0 | 0.9 ± 0.0 | 5.3 ± 0.3 | 7.0 ± 0.1 | 8.9 ± 0.3 | 11.3 ± .7 |
| Day 10 | 0.0 | 1.3 ± 0.1 | 1.2 ± 0.1 | 4.0 ± 0.1 | 5.9 ± 0.4 | 5.0 ± 0.6 | 6.4 ± 0.3 |
| Day 11 | 0.0 | 1.3 ± 0.1 | 1.2 ± 0.1 | 2.8 ± 0.1 | 5.0 ± 0.6 | 3.6 ± 0.1 | 4.8 ± 0.5 |
| Day 12 | 0.0 | 1.2 ± 0.1 | 1.1 ± 0.0 | 2.0 ± 0.1 | 4.2 ± 0.4 | 2.7 ± 0.1 | 3.3 ± 0.1 |
| Day 15* | 0.0 | 2.3 ± 0.2 | 2.2 ± 0.1 | 2.8 ± 0.1 | 7.2 ± 0.6 | 6.8 ± 0.0 | 7.1 ± 0.1 |
|  | 0.0 | 1.1 ± 0.1 | 1.1 ± 0.0 | 0.9 ± 0.0 | 2.7 ± 0.2 | 2.6 ± 0.1 | 2.7 ± 0.0 |
| Day 16 | 0.0 | 1.0 ± 0.1 | 1.1 ± 0.1 | 0.7 ± 0.0 | 2.4 ± 0.1 | 2.3 ± 0.1 | 2.4 ± 0.1 |
| Day 17 | 0.0 | 1.0 ± 0.1 | 0.9 ± 0.0 | 0.6 ± 0.1 | 2.1 ± 0.2 | 2.3 ± 0.1 | 2.3 ± 0.3 |
| Day 18 | 0.0 | 1.1 ± 0.1 | 1.1 ± 0.1 | 0.6 ± 0.0 | 1.8 ± 0.2 | 2.0 ± 0.1 | 2.0 ± 0.1 |
| Day 19 |  |  |  |  |  |  |  |
| Day 22* | 0.0 | 1.6 ± 0.2 | 1.7 ± 0.1 | 1.4 ± 0.1 | 2.8 ± 0.3 | 4.5 ± 0.0 | 4.5 ± 0.1 |
|  | 0.0 | 0.8 ± 0.1 | 0.9 ± 0.0 | 0.8 ± 0.0 | 1.7 ± 0.0 | 2.1 ± 0.1 | 2.4 ± 0.3 |
| Day 23 | 0.0 | 0.7 ± 0.1 | 0.8 ± 0.1 | 0.5 ± 0.0 | 1.0 ± 0.2 | 1.6 ± 0.1 | 1.6 ± 0.1 |
| Day 24 | 0.0 | 0.8 ± 0.1 | 0.8 ± 0.1 | 0.7 ± 0.1 | 1.1 ± 0.1 | 1.7 ± 0.2 | 1.8 ± 0.1 |
| Day 25 | 0.0 | 0.8 ± 0.1 | 0.8 ± 0.1 | 0.7 ± 0.1 | 1.1 ± 0.1 | 1.6 ± 0.1 | 1.7 ± 0.2 |
| Day 26 |  |  |  |  |  |  |  |
| Day 29* | 0.0 | 1.2 ± 0.1 | 1.3 ± 0.1 | 1.0 ± 0.1 | 1.9 ± 0.1 | 3.1 ± 0.1 | 3.3 ± 0.1 |
|  | 0.0 | 0.8 ± 0.1 | 0.8 ± 0.1 | 0.6 ± 0.0 | 1.3 ± 0.1 | 1.6 ± 0.1 | 1.8 ± 0.1 |
| Day 30 |  |  |  |  |  |  |  |

*Indicates when pellets were left over the weekend, i.e, for longer than one day.

sealants may well provide longer term fluoride release than the seven day burst effect reported by Cooley et al (1990). In orthodontics, it could be added to composite bonding materials to cement bands and brackets. Addition to orthodontic bonding materials would be of great value in prevention of the widespread enamel demineralization that is observed around orthodontic bands and brackets (Shannon & West, 1979; Chadwick, 1994; Chadwick & Gordon, 1995). Again the use in orthodontics would be of considerable benefit as the majority of malocclusions requiring fixed appliance therapy are of two years duration. Hence, if one of the glass devices could be attached to a band or bracket or the fluoride glass incorporated within the bonding material, then protection for the duration of the orthodontic treatment would be ensured. It may also be possible to incorporate the fluoride glass powder within acrylic resin for construction of removable orthodontic appliances. Boyd (1993) compared the effectiveness of a 1100 ppm fluoride toothpaste used alone, or together with a 0.05% sodium fluoride daily rinse or a 0.4% stannous fluoride gel applied twice daily, in controlling the decalcification that accompanies orthodontic treatment. Boyd's results indicated that twice daily use of the fluoride toothpaste and either a once-daily fluoride rinse or a twice-daily fluoride gel provided additional protection against decalcification beyond that achieved with fluoride toothpaste alone. Similarly, in prosthetic dentistry, the use of the fluoride glass powder in acrylic will have potential for fluoride release around abutment teeth. In periodontology, the application of this form of fluoride within a resin varnish may be of benefit in the treatment of exposed sensitive root dentine. A role in oral surgery may also be possible, for example the prior coating of implants with this material. Patients suffering from xerostomia from a variety of causes are at greater caries-risk, and therefore, these devices would have an important caries-preventive role for this group of patients. Roots dentine caries is a common occurrence in the elderly, and these devices would also have an important preventive role.

EXAMPLE 6

Further glass compositions according to the present invention were studied for their composition parameters. The results are shown in FIG. 5 of the accompanying drawings. The glass compositions are labeled 1–82 respectively and are shown in order of the solubility. The glass composition chosen for a particular application will depend upon the duration and amount of fluoride release required. Glass compositions experiencing devitrification or phase separation (indicated by 1–5, with 5 having the most extensive devitrification or phase separation) do not form true glasses.

Table XI below shows the overall range of compositions studied, the compositions that formed good glasses, the compositions that provided the preferred solubility and the range that provide both good glass and the preferred solubility.

TABLE XI

| | RANGES | | | | | | | |
|---|---|---|---|---|---|---|---|---|
| | OVERALL RANGE OF COMPOSITIONS | | GOOD GLASS | | PREFERRED | | GOOD GLASS | |
| | MIN. | MAX. | MIN. | MAX. | MIN. | MAX. | MIN. | MAX |
| Na | 6.81 | 24.25 | 11.86 | 24.25 | 6.81 | 23.62 | 11.86 | 22.6 |
| P | 17.09 | 22.37 | 18.08 | 22.37 | 17.09 | 22.37 | 18.08 | 22.37 |
| Al | 3.39 | 8.87 | 4.31 | 8.87 | 4.31 | 7.48 | 4.31 | 7.48 |
| F | 16.22 | 24.5 | 16.22 | 24.1 | 16.27 | 22.87 | 16.27 | 22.87 |
| O | 26.43 | 34.48 | 27.87 | 34.48 | 26.43 | 34.48 | 27.87 | 34.48 |
| K | 0 | 21.36 | 0 | 13.87 | 0 | 21.36 | 0 | 13.87 |
| Ca | 0 | 5.75 | 0 | 5.75 | 0 | 5.75 | 0 | 5.75 |
| Mg | 0 | 5.6 | 0 | 2.61 | 0 | 2.61 | 0 | 2.61 |
| Na + K | 17.73 | 28.17 | 19.08 | 25.78 | 19.08 | 28.17 | 19.08 | 25.73 |
| F Retention | 44.4 | 65.54 | 44.4 | 65.54 | 47.74 | 65.54 | 47.94 | 65.54 |
| Solubility | 45 | 10429 | 45 | 10429 | 100 | 1006 | 100 | 1006 |
| F Analyzed | 7.8 | 14.2 | 7.8 | 14.2 | 7.8 | 13.5 | 7.8 | 13.5 |

EXAMPLE 7

Samples 1, 13 and 31 of Example 6 were investigated to determine the effect of varying melt time and temperature on the solubility and fluoride retention of the composition. Table XII below illustrates the results of the investigations:

TABLE XII

EFFECT OF VARYING MELT TIME AND TEMPERATURE

| Code | Na | P | Al | F | O | K | Ca | Mg | TO T. | Na + K | F Anal. | Sol. | Ret. | Melt Temp | Melt Time |
|---|---|---|---|---|---|---|---|---|---|---|---|---|---|---|---|
| 1 | 21.23 | 20.67 | 6.76 | 19.48 | 31.86 | 0 | 0 | 0 | 100 | 21.23 | 8.9 | 115 | 45.7 | 650 | 45 |
| 1 | 21.23 | 20.67 | 6.76 | 19.48 | 31.86 | 0 | 0 | 0 | 100 | 21.23 | 8.1 | 116 | 41.6 | 650 | 90 |
| 1 | 21.23 | 20.67 | 6.76 | 19.48 | 31.86 | 0 | 0 | 0 | 100 | 21.23 | 9.6 | 98 | 49.3 | 700 | 45 |
| 1 | 21.23 | 20.67 | 6.76 | 19.48 | 31.86 | 0 | 0 | 0 | 100 | 21.23 | 8.1 | 94 | 41.9 | 700 | 90 |
| 1 | 21.23 | 20.67 | 6.76 | 19.48 | 31.86 | 0 | 0 | 0 | 100 | 21.23 | 9.6 | 95 | 49.3 | 750 | 45 |
| 1 | 21.23 | 20.67 | 6.76 | 19.48 | 31.86 | 0 | 0 | 0 | 100 | 21.23 | 7.4 | 77 | 38.0 | 750 | 90 |
| 13 | 22.72 | 20.31 | 6.11 | 19.56 | 31.3 | 0 | 0 | 0 | 100 | 22.72 | 9.3 | 1209 | 47.5 | 650 | 45 |
| 13 | 22.72 | 20.31 | 6.11 | 19.56 | 31.3 | 0 | 0 | 0 | 100 | 22.72 | 8.4 | 984 | 42.9 | 650 | 90 |
| 13 | 22.72 | 20.31 | 6.11 | 19.56 | 31.3 | 0 | 0 | 0 | 100 | 22.72 | 10 | 1134 | 51.1 | 700 | 45 |
| 13 | 22.72 | 20.31 | 6.11 | 19.56 | 31.3 | 0 | 0 | 0 | 100 | 22.72 | 8.1 | 892 | 41.4 | 700 | 90 |
| 13 | 22.72 | 20.31 | 6.11 | 19.56 | 31.3 | 0 | 0 | 0 | 100 | 22.72 | 8.7 | 1180 | 44.5 | 750 | 45 |
| 13 | 22.72 | 20.31 | 6.11 | 19.56 | 31.3 | 0 | 0 | 0 | 100 | 22.72 | 7.8 | 822 | 39.9 | 750 | 90 |
| 31 | 19.27 | 19.95 | 4.79 | 18.74 | 30.75 | 4.49 | 1.14 | 0.87 | 100 | 23.76 | 9.2 | 570 | 49.1 | 650 | 45 |
| 31 | 19.27 | 19.95 | 4.79 | 18.74 | 30.75 | 4.49 | 1.14 | 0.87 | 100 | 23.76 | 10.1 | 440 | 53.9 | 650 | 90 |
| 31 | 19.27 | 19.95 | 4.79 | 18.74 | 30.75 | 4.49 | 1.14 | 0.87 | 100 | 23.76 | 10 | 508 | 53.4 | 700 | 45 |
| 31 | 19.27 | 19.95 | 4.79 | 18.74 | 30.75 | 4.49 | 1.14 | 0.87 | 100 | 23.76 | 9.2 | 379 | 49.1 | 700 | 90 |

TABLE XII-continued

EFFECT OF VARYING MELT TIME AND TEMPERATURE

| Code | Na | P | Al | F | O | K | Ca | Mg | TO T. | Na + K | F Anal. | Sol. | Ret. | Melt Temp | Melt Time |
|------|------|------|------|------|------|------|------|------|-----|-------|------|-----|------|------|------|
| 31 | 19.27 | 19.95 | 4.79 | 18.74 | 30.75 | 4.49 | 1.14 | 0.87 | 100 | 23.76 | 10.2 | 452 | 54.4 | 750 | 45 |
| 31 | 19.27 | 19.95 | 4.79 | 18.74 | 30.75 | 4.49 | 1.14 | 0.87 | 100 | 23.76 | 8.9 | 352 | 47.5 | 750 | 90 |

The invention claimed is:

1. A glass composition for treatment of dental caries, the glass composition being formed by combining and melting a phosphorus oxide and at least one of Na, K, Li, or Al in oxide and/or fluoride form, the glass composition comprising the following general empirical formula, expressed in weight percent of each element:

P: 16–24
F: 5–30
O: 20–40 and at least one of Na, K, Li, or Al in an amount up to a total of 40% by weight, wherein the glass composition releases a therapeutically effective amount of water soluble fluoride ions over time when exposed to saliva in a person's mouth.

2. The glass composition as claimed in claim 1, wherein at least one of a fluoride or an oxide of at least one glass modifier is included in the glass composition.

3. The glass composition as claimed in claim 2, wherein the fluoride of at least one glass modifier is selected from the group consisting of aluminum fluoride, sodium hydrogen fluoride, sodium fluoride, calcium fluoride, magnesium fluoride, potassium fluoride, and mixtures thereof.

4. The glass composition as claimed in claim 2, the glass composition further comprising one or more other glass modifiers.

5. The glass composition as claimed in claim 4, wherein the one or more other glass modifiers comprise at least one of calcium, magnesium or zinc.

6. The glass composition as claimed in claim 4, wherein the one or more other glass modifiers are included in an amount of up to 10% by weight.

7. The glass composition as claimed in claim 1, wherein the glass composition includes a combined weight percent of at least 16% of sodium and potassium.

8. The glass composition as claimed in claim 1, wherein aluminum is included in the glass composition in an amount of at least 3% by weight.

9. The glass composition as claimed in claim 1, wherein at least 25% by weight oxygen is included in the glass composition.

10. The glass composition as claimed in claim 1, wherein the phosphorus is included in an amount of 18–23% by weight.

11. The glass composition as claimed in claim 1, wherein at least 12% by weight of fluoride is included in the glass composition.

12. The glass composition as claimed in claim 1, wherein the glass composition provides a fluoride retention of at least 45% at a melting temperature of 650° over 45 minutes.

13. The glass composition as claimed in claim 1, wherein the glass composition has a solubility in a range of 5–10,000.

14. The glass composition as claimed in 1, wherein the glass composition is provided in powder form and has a solubility in a range of 5 to 100.

15. The glass composition as claimed in claim 14, wherein the glass composition in powder form is incorporated in a dental restorative material.

16. The glass composition as claimed in claim 15, wherein the dental restorative material is selected from the group consisting of dental amalgams, fissure sealant resins, and composite bonding materials.

17. The glass composition as claimed in claim 1, wherein the glass composition is attached to a tooth using dental cement.

18. A method for treatment of dental caries, the method comprising attaching a glass composition to a tooth to provide a fluoride releasing device and allowing the glass composition to release a therapeutically effective amount of water soluble fluoride ions over time when exposed to saliva in a person's mouth, the glass composition being formed by combining and melting a phosphorus oxide and at least one of Na, K, Li, or Al in oxide and/or fluoride form and comprising the following general empirical formula, expressed in weight percent of each element:

P: 16–24
F: 5–30
O: 20–40 and at least one of Na, K, Li, or Al in an amount up to a total of 40% by weight.

19. A method as claimed in claim 18, further comprising attaching the glass composition to the tooth using dental cement.

20. A method as claimed in claim 18, wherein the glass composition is provided in powder form and incorporated into a dental restorative material.

21. The glass composition as claimed in claim 1, wherein the glass composition further includes at least one of boron or silicon.

22. The glass composition as claimed in claim 21, wherein the boron or silicon are included in an amount up to 5% by weight.

23. A method as claimed in claim 18, wherein the glass composition further includes at least one of boron or silicon in an amount up to 5% by weight.

24. A glass composition suitable for use in treating dental caries comprising, on an empirical basis, at least 16% by weight phosphorus, at least 25% by weight oxygen, 5–30% by weight fluoride, and at least one of sodium, potassium, lithium or aluminum in an amount up to a total of 40% by weight, wherein the glass composition is formed by combining and melting a phosphorus oxide and at least one of sodium, potassium, lithium or aluminum in oxide and/or fluoride form, wherein the glass composition releases a therapeutically effective amount of water soluble fluoride ions over time when exposed to saliva in a person's mouth.

25. A glass composition as claimed in claim 24, wherein the glass composition is formed using at least one of a fluoride or an oxide of at least one glass modifier.

26. A glass composition as claimed in claim 25, wherein the fluoride of at least one glass modifier comprises at least one of aluminum fluoride, sodium hydrogen fluoride, sodium fluoride, calcium fluoride, magnesium fluoride, or potassium fluoride.

27. A glass composition as claimed in claim 24, further comprising at least one glass modifier.

28. A glass composition as claimed in claim 27, wherein the glass modifier comprises at least one of calcium, magnesium or zinc.

29. A glass composition as claimed in claim 27, wherein the glass modifier is included in an amount of up to 10% by weight.

30. A glass composition as claimed in claim 24, wherein the glass composition comprises at least one of sodium or potassium in a combined amount of at least 16% by weight.

31. A glass composition as claimed in claim 24, wherein the glass composition comprises at least one of sodium or potassium in a combined amount in a range of 19–26% by weight.

32. A glass composition as claimed in claim 24, wherein the glass composition comprises aluminum in an amount of at least 3% by weight.

33. A glass composition as claimed in claim 24, wherein the glass composition comprises aluminum in an amount in a range of 4–10% by weight.

34. A glass composition as claimed in claim 24, wherein the oxygen is included in an amount in a range of 25–35% by weight.

35. A glass composition as claimed in claim 24, wherein the phosphorus is included in an amount in a range of 17–23% by weight.

36. A glass composition as claimed in claim 24, wherein the fluoride is included in an amount of at least 12% by weight.

37. A glass composition as claimed in claim 24, wherein the fluoride is included in an amount in a range of 15–25% by weight.

38. A glass composition as claimed in claim 24, wherein the glass composition provides a fluoride retention of at least 45% at a melting temperature of 650° over 45 minutes.

39. A glass composition as claimed in claim 24, wherein the glass composition provides a fluoride retention of at least 60% at a melting temperature of 650° over 45 minutes.

40. A glass composition as claimed in claim 24, wherein the glass composition has a solubility in a range of 5 to 10,000.

41. A glass composition as claimed in claim 24, wherein the glass composition has a solubility in a range of 100 to 1100.

42. A glass composition as claimed in claim 24, wherein the glass composition is in powder form and has a solubility in a range of 5 to 100.

43. A glass composition as claimed in claim 42, wherein the glass composition in powder form comprises a portion of a dental restorative material.

44. A glass composition as claimed in claim 43, wherein the dental restorative material is selected from the group consisting of dental amalgams, fissure sealant resins, and composite bonding materials.

45. A glass composition as claimed in claim 24, wherein the glass composition is sized and configured for attachment to a tooth.

46. A glass composition as claimed in claim 24, further including at least one of boron or silicon.

47. A glass composition as claimed in claim 46, wherein the boron or silicon are included in an amount up to 5% by weight.

48. A glass composition as claimed in claim 24, wherein the glass composition has a solubility rate so as to continuously release fluoride for a period of 12–36 months when attached to a person's tooth.

49. A glass composition suitable for use in treating dental caries comprising, on an empirical basis, 18–23% by weight phosphorus, 20–40% by weight oxygen, 5–30% by weight fluoride, and at least one of sodium, potassium, lithium or aluminum in an amount up to a total of 40% by weight, wherein the glass composition is formed by combining and melting a phosphorus oxide and at least one of sodium, potassium, lithium or aluminum in oxide and/or fluoride form, wherein the glass composition releases a therapeutically effective amount of water soluble fluoride ions over time when exposed to saliva in a person's mouth.

50. A glass composition suitable for use in treating dental caries comprising, on an empirical basis, 16–24% by weight phosphorus, 20–40% by weight oxygen, 5–30% by weight fluoride, at least one of sodium, potassium, lithium or aluminum in an amount up to a total of 40% by weight, and at least one of calcium, magnesium, or zinc in an amount of up to a total of 10% by weight, wherein the glass composition is formed by combining and melting a phosphorus oxide, at least one of sodium, potassium, lithium or aluminum in oxide and/or fluoride form, and at least one of calcium, magnesium, or zinc in oxide and/or fluoride form, wherein the glass composition releases a therapeutically effective amount of water soluble fluoride ions over time when exposed to saliva in a person's mouth.

* * * * *

UNITED STATES PATENT AND TRADEMARK OFFICE
CERTIFICATE OF CORRECTION

PATENT NO. : 7,175,833 B1 Page 1 of 1
APPLICATION NO. : 10/069143
DATED : February 13, 2007
INVENTOR(S) : Brian Algar It is certified that error appears in the above-identified patent and that said Letters Patent is hereby corrected as shown below:

<u>Col. 7</u>
Line 44 change "tem" to --the system--

Signed and Sealed this

Twenty-second Day of July, 2008

JON W. DUDAS
*Director of the United States Patent and Trademark Office*